United States Patent [19]

Luzzio et al.

[11] Patent Number: 5,223,506
[45] Date of Patent: Jun. 29, 1993

[54] CYCLIC ANTITUMOR COMPOUNDS

[75] Inventors: Michael J. Luzzio; Jeffrey M. Besterman, both of Durham; Michael G. Evans, Pittsboro; M. Ross Johnson; Milana Dezube, both of Chapel Hill; Salvatore Profeta, Jr., Durham, all of N.C.

[73] Assignee: Glaxo Inc., Research Triangle Park, N.C.

[21] Appl. No.: 710,230

[22] Filed: Jun. 4, 1991

[51] Int. Cl.$^5$ .................. A61K 31/44; C07D 471/00
[52] U.S. Cl. .................. 514/279; 514/280; 514/285; 546/41; 546/48; 546/61
[58] Field of Search .................. 546/61, 48, 41; 514/285, 280, 279

[56] References Cited

U.S. PATENT DOCUMENTS 3,647,801  3/1972  Petrzilka .................. 546/41

OTHER PUBLICATIONS

*Tetrahedron*, 29, 359-362 (1973).
*J. Ind. Chem. Soc.*, 7, 638-645.
*Synthesis*, 6, 458-561 (1989).
*Chem. Abstracts*, 112, No. 7, (1990).
*Tetrahedron*, 46, 2445-2452 (1990).
*J. Med. Chem.*, 14, 1116-1118 (1971).
*J. Heterocyclic Chem.*, 10, 1035-1038 (1973).
*J. Med. Chem.*, 33, 972-978 (1990).
A. Lehninger, Principles of Biochemistry, 813, Worth Publishers, New York, 1982.
F. Liu, DNA Topoisomerases, CRC Critical Review in Biochemistry, 1-24, 15 1983.
H. Vosberg, DNA Topoisomerases: Enzymes that control Conformation, Current Topics in Microbiology and Immunology 19, 1985.
E. Nelson, et al., Proc. Nat. Acad Sci., USA, 81, 1361 1984.
C. Chang, "Friedlander Synthesis of Quinolines", Organic reactiond, 28, 37-201, John Wiley, New York 1982 pp. 92-99 vol. 28.

T. Green, Protective Group in Organic Chemistry Chap 3 John Wiley, New York 1981.
A. I. Vogel, Practical Organic Chemistry, 4th Ed., 773 Longmans, London 1978.
Y. Hsiang, et al., J. Biol. Chem., 260:14873-14878 1985.
Y. Hsiang, et al., Cancer research, 49:4385-4389 1989.
Jaxel, et al Cancer Research, 49:1465-1469.
DNA Topoisomerase in Cancer, M. Potmesil, et al., Ed's., Oxford University Press (1991).

*Primary Examiner*—Marianne M. Cintins
*Assistant Examiner*—Catherine S. Kilby Scalzo
*Attorney, Agent, or Firm*—Charles T. Joyner

[57] ABSTRACT

The present invention relates to certain substituted tetracyclic fused quinoline derivatives of formula (I):

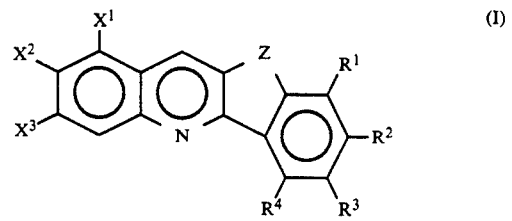

(I)

wherein:

$R^1$ is hydrogen, hydroxy, fluoro, chloro, bromo, iodo, methoxy or amino;

$R^2$ is hydrogen, hydroxy, methoxy or amino;

$R^3$ is hydrogen, hydroxy, methoxy, methoxymethoxy, amino, —OCONH$_2$, [2(5H)-3,4-dihydro-3-oxyfuranone], 2-hydroxyethoxy, 2-aminoethoxy, 3-hydroxypropoxy or 3-aminopropoxy; or taken together with $R^2$ or $R^4$, methylenedioxy or ethylenedioxy;

$R^4$ is hydrogen, hydroxy or amino;

Z is —CH$_2$—, —O— or —NH—; and a) $X^1$ is hydrogen; $X^2$ is hydrogen, hydroxy, fluoro, chloro, bromo, iodo or methoxy; and $X^3$ is hydrogen or hydroxy; or b) $X^2$ taken together with $X^3$ is methylenedioxy or ethylenedioxy, and $X^1$ is hydrogen or a pharmaceutically acceptable salt thereof provided that:

i) at least one of $R^1$ through $R^4$ is other than hydrogen;
ii) when $R^1$ is methoxy, $R^2$ is hydroxy or methoxy, $R^3$ is hydrogen or methoxy and $R^4$ is hydrogen;
iii) when $R^2$ is hydroxy, methoxy or amino, $R^3$ is hydrogen, hydroxy or methoxy, and $R^4$ is hydrogen;
iv) when $R^4$ is hydroxy or amino, $R^1$ and $R^3$ are hydrogen and $R^2$ is hydroxy or amino; and.
v) when $R^1$ is fluoro, chloro, iodo or amino, $R^2$ is hydrogen, hydroxy or methoxy, $R^3$ is hydrogen, hydroxy or methoxy and $R^4$ is hydrogen and the use of these compounds as topoisomerase inhibitors and antitumor agents.

20 Claims, No Drawings

CYCLIC ANTITUMOR COMPOUNDS

The present invention relates to certain substituted tetracyclic fused quinoline derivatives which have topoisomerase inhibition and antitumor activity.

BACKGROUND OF THE INVENTION

Before a living cell can reproduce, its DNA strands must unwind from their normal coiled configurations and assume a topology favorable for replication. To allow this unwinding the enzymes known as topoisomerases serve to introduce "swivels" in DNA strands. Without such a mechanism the DNA could not replicate, and hence the cell could not reproduce and proliferate. For detailed explanations of the topoisomerase function see A. Lehninger, *Principles of Biochemistry*, 813, Worth Publishers, New York (1982); L. F. Liu, "DNA Topoisomerases," *CRC Critical Review in Biochemistry*, 1–24, 15 (1983) and H Vosberg, "DNA Topoisomerases: Enzymes that Control DNA Conformation," *Current Topics in Microbiology and Immunology*, 19, Springer-Verlag, Berlin (1985). It has been recognized for some time that cell proliferation might be controlled by inhibition of topoisomerases and that such control might be particularly useful in halting the spread of tumors and related malignancies and ultimately destroying them. See E. Nelson, et al., *Proc. Nat. Acad. Sci. U.S.A.*, 81, 1361 (1984).

On the basis of mechanism of action, topoisomerases have been categorized as Type I and Type II (often referred to as "topo I" and "topo II", respectively). The clinically useful antitumor agents adriamycin, mitoxantrone, etoposide and m-AMSA have been reported to work by inhibiting the function of Type II topoisomerase. Camptothecin, a natural product antitumor agent, has been found to inhibit the function of Type I topoisomerase as have certain synthetic camptothecin analogs (see Wall, et al., U.S. Pat. No. 4,894,456). It is now believed that a compound which could effectively inhibit the functions of either or both Type I and Type II would be a potent antitumor agent.

SUMMARY OF THE INVENTION

One aspect of the present invention is the genus of the compounds of formula (I),

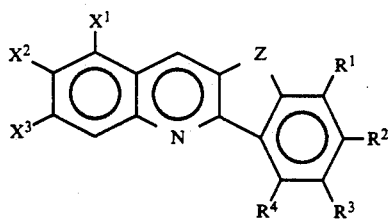

wherein:
$R^1$ is hydrogen, hydroxy, fluoro, chloro, bromo, iodo, methoxy or amino;
$R^2$ is hydrogen, hydroxy, methoxy or amino;
$R^3$ is hydrogen, hydroxy, methoxy, methoxymethoxy, amino, —OCONH$_2$, [2(5H)-3,4-dihydro-3-oxyfuranone], 2-hydroxyethoxy, 2-aminoethoxy, 3-hydroxypropoxy or 3-aminopropoxy; or taken together with $R^2$ or $R^4$, methylenedioxy or ethylenedioxy;
$R^4$ is hydrogen, hydroxy or amino;
Z is —CH$_2$—, —O— or —NH—; and
a) $X^1$ is hydrogen; $X^2$ is hydrogen, hydroxy, fluoro, chloro, bromo, iodo or methoxy; and $X^3$ is hydrogen or hydroxy; or
b) $X^2$ taken together with $X^3$ is methylenedioxy or ethylenedioxy, and $X^1$ is hydrogen or a pharmaceutically acceptable salt thereof provided that:
i) at least one of $R^1$ through $R^4$ is other than hydrogen;
ii) when $R^1$ is methoxy, $R^2$ is hydroxy or methoxy, $R^3$ is hydrogen or methoxy and $R^4$ is hydrogen;
iii) when $R^2$ is hydroxy, methoxy or amino, $R^3$ is hydrogen, hydroxy or methoxy, and $R^4$ is hydrogen;
iv) when $R^4$ is hydroxy or amino, $R^1$ and $R^3$ are hydrogen and $R^2$ is hydroxy or amino; and
v) when $R^1$ is fluoro, chloro, iodo or amino, $R^2$ is hydrogen, hydroxy or methoxy, $R^3$ is hydrogen, hydroxy or methoxy and $R^4$ is hydrogen.

As will be understood by those skilled in the art, pharmaceutically acceptable salts include, but are not limited to salts with inorganic acids such hydrochloride, sulfate, phosphate, diphosphate, hydrobromide and nitrate or salts with an organic acid such as malate, maleate, fumarate, tartrate, succinate, citrate, acetate, lactate, methansulfonate, p-toluenesulfonate, palmoate, salicylate and stearate.

Another aspect of the invention is a method of inhibiting topoisomerase Types I and II in mammalian cells comprising contacting these enzymes with a topoisomerase inhibiting amount of a compound of formula (I), and a method of treating a tumor in a mammal comprising administering to a mammal bearing a tumor, an effective antitumor amount of a compound of formula (I). A further aspect comprises pharmaceutical formulations containing a compound of formula (I) as an active ingredient. Novel chemical intermediates used in the synthesis, as taught herein, of the compounds of formula (I) are also within the scope of the present invention.

DETAILED DESCRIPTION OF THE INVENTION

Particular compounds of formula (I) are those wherein:
A. $X^2$ taken together with $X^3$ is methylenedioxy
B. Z is —CH$_2$—
C. Z is —O—
D. Z is —NH—
E. $X^2$ is hydroxy, chloro or methoxy; and $X^3$ is hydrogen or hydroxy,
including combinations of the above, e.g., (A and B), (A and C), (B and E), (A and D), (D and E) and (C and E).
Specific compounds of formula (I) are:

| Compound/ Example Number | Compound Name |
|---|---|
| 1. | 8-methoxy-10H-1,3-dioxolo[4,5-g]indeno[1,2-b]quinoline |
| 2. | 7,8,9-trimethoxy-10H-1,3-dioxolo[4,5-g]indeno[1,2-b]quinoline |
| 3. | 7,8-dimethoxy-10H-1,3-dioxolo[4,5-g]indeno[1,2-b]quinoline |
| 4. | 7-methoxy-10H-1,3-dioxolo[4,5-g]indeno[1,2-b]quinoline |
| 5. | 7,9-dimethoxy-8-hydroxy-10H-1,3-dioxolo[4,5-g]indeno[1,2-b]quinoline |
| 6. | 6,7(1,4-dioxano)-10H-1,3-dioxolo[4,5-g]indeno[1,2-b] |

| Compound/ Example Number | Compound Name |
|---|---|
| 7. | 7,8(1,4-dioxano)-10H-1,3-dioxolo[4,5-g]indeno[1,2-b]quinoline |
| 8a. | 7-methoxymethoxy-8-methoxy-10H-1,3-dioxolo[4,5-g]indeno[1,2-b]quinoline |
| 8b. | 7-hydroxy-8-methoxy-10H-1,3-dioxolo[4,5-g]indeno[1,2-b]quinoline |
| 9. | 7-(2-aminoethoxy)-8-methoxy-10H-1,3-dioxolo[4,5-g]indeno[1,2-b]quinoline |
| 10. | 7-(2-hydroxyethoxy)-8-methoxy-10H-1,3-dioxolo[4,5-g]indeno[1,2-b]quinoline |
| 11. | 8-methoxy-9-hydroxy-10H-1,3-dioxolo[4,5-g]indeno[1,2-b]quinoline |
| 12. | (+/−)7-[2(5H)-3,4-dihydro-3-oxyfuranone]-8-methoxy-10H-1,3-dioxolo[4,5-g]indeno[1,2-b]quinoline |
| 13. | 7-n-methylcarbamoyl-8-methoxy-10H-1,3-dioxolo[4,5-g]indeno[1,2-b]quinoline |
| 14b. | 7-methoxy-8-hydroxy-10H-1,3-dioxolo[4,5-g]indeno[1,2-b]quinoline |
| 15b. | 7,8-dihydroxy-10H-1,3-dioxolo[4,5-g]indeno[1,2-b]quinoline |
| 16b. | 8-hydroxy-10H-1,3-dioxolo[4,5-g]indeno[1,2-b]quinoline |
| 17. | 2,3-dimethoxy-11H-indeno-8-chloro-[1,2-b]quinoline |
| 18. | 2,3-dimethoxy-11H-indeno-[1,2-b]quinolin-8-ol |
| 19. | 2,3-dimethoxy-11H-indeno-8-methoxy-[1,2-b]quinolin-7-ol |
| 20. | 2,3-dimethoxy-11H-indeno-[1,2-b]quinolin-8-ol |
| 21. | 2-hydroxy-3-methoxy-11H-indeno-[1,2-b]quinolin-8-ol |
| 22. | 2-methoxy-3-hydroxy-11H-indeno-[1,2-b]quinolin-8-ol |
| 23. | 2-methoxy-11H-indeno[1,2-b]quinolin-8-ol |
| 24. | 2-hydroxy-11H-indeno[1,2-b]quinolin-8-ol |
| 25. | 7,8-dimethoxybenzofuro[3,2-b]quinolin-2-ol |
| 26. | 7,8-dimethoxybenzofuro-1,3-dioxolo[3,2-b]quinoline |
| 27. | 8-methoxybenzofuro-1,3-dioxolo[3,2-b]quinoline |
| 28. | 6,8-dihydroxybenzofuro-1,3-dioxolo[3,2-b]quinoline |
| 29. | 6,8-dihydroxybenzofuro-[3,2-b]quinolin-2-ol |

As shown in Scheme (I):

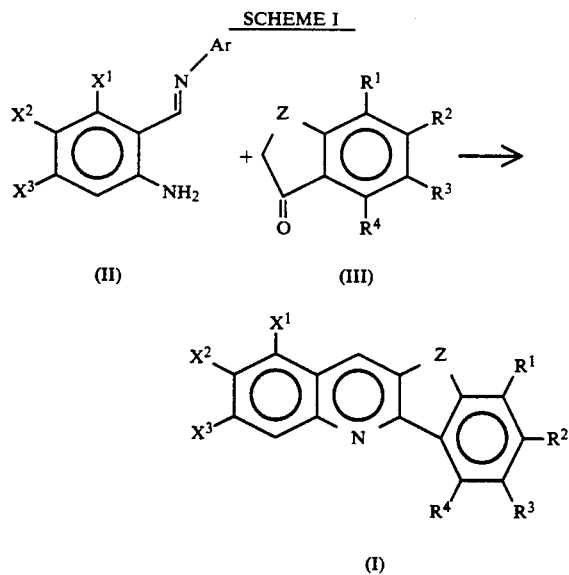

a compound of formula (II), wherein $X^1$ through $X^3$ are as defined for formula (I), and Ar is a $C_{6-12}$, one or two ring, substituted or unsubstituted, aromatic group (e.g., phenyl or 4-toluyl), may be reacted with a compound of formula (III), wherein $R^1$ through $R^4$ and Z are as defined for formula (I), to yield a corresponding compound of formula (I). This reaction may be conveniently carried out in a polar solvent system, for example, water, $(C_{1-4})$ alkanol, $(C_{2-4})$ alkylene diol or mixture thereof (e.g., water/ethanol) in the presence of a compatible strong mineral acid or alkali metal hydroxide base (e.g., sulfuric acid or sodium hydroxide) at a temperature in the range of from about 50° C. to about 150° C. See C. Cheng, "Friedländer Synthesis of Quinolines," Organic Reactions, 28, 37–201, John Wiley, New York (1982).

A compound of formula (I) prepared by this reaction scheme may be purified by conventional methods of the art, e.g., chromatography, distillation or crystallization.

Where $R^1$, $R^2$, $R^3$ or $R^4$ of a compound of formula (III); or $X^2$ or $X^3$ of a compound of formula (II) are base sensitive hydroxy, it is preferable to protect these functionalities by converting them into protected derivatives, herein referred to collectively as "protected hydroxy functions" or "protected hydroxy." For example, hydroxy may be converted to an ether, e.g., alkoxyalkyl ethers or benzyl ethers, by methods known in the art, such as those taught in T. Green, Protective Groups in Organic Chemistry, Chap. 3, John Wiley, New York (1981). Protected hydroxy functions are stable to bases, compatible with basic catalysis conditions if used in the reaction of Scheme (I) and can conveniently be reconverted to the corresponding hydroxys by conventional techniques, such as those taught by T. Green, supra, e.g., by treatment with acid, following completion of the reaction of Scheme (I).

Likewise, where $R^1$ and/or $R^3$ are the acid or base sensitive amino, it is preferable to the protect the amino function by converting it into a protected amino derivative (herein, "protected amino"), e.g., an amide or a carbamate, by methods known in the art, such as those methods taught in T. Green, supra, Chap. 7. Protected amino functions are selected to be compatible with acidic or basic catalysis conditions used for the reaction of Scheme (I) and can conveniently be reconverted to amino by conventional techniques, such as those taught by T. Green, supra, e.g., hydrogenation using a palladium on carbon catalysis, after completion of the reaction of Scheme (I).

Compounds of formula (I) may be convered to other compounds of formula (I). For example a compound of formula (I) bearing a methoxymethoxy function can be converted to a corresponding compound of formula (I) bearing an hydroxy function by treatment with a $(C_{1-4})$ alkanoic acid, e.g., refluxing in acetic acid.

The compounds of formulas (II) and (III) are either available commercially or may be prepared by methods of the art. For example, the compounds of formula (II) may be prepared by the methods taught by C. Cheng, supra, and the compounds of formula (III) may be prepared by the method taught by A. I. Vogel, Practical Organic Chemistry, 4th Ed., 773, Longmans, London (1978).

The intermediate compounds of formula (IA) having at least one protected function

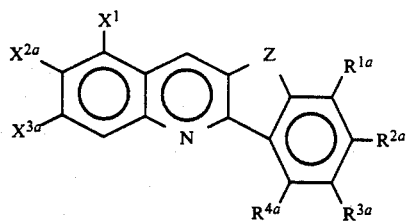

(IA)

wherein:

$R^{1a}$ is hydrogen, protected hydroxy, fluoro, chloro, bromo, iodo, methoxy or protected amino;

$R^{2a}$ is hydrogen, protected hydroxy, methoxy or protected amino;

$R^{3a}$ is hydrogen, protected hydroxy, methoxy, protected amino, —OCONH$_2$, [2(5H)-3,4-dihydro-3-oxyfuranone], 2-hydroxyethoxy, 2-aminoethoxy, 3-hydroxypropoxy or, taken together with $R^{2a}$ or $R^{4a}$, methylenedioxy or ethylenedioxy;

$R^{4a}$ is hydrogen, protected hydroxy or protected amino;

Z is —CH$_2$—, —O— or —NH—; and a) $X^1$ is hydrogen; $X^{2a}$ is hydrogen, protected hydroxy, F, Cl, Br, I or methoxy; $X^{3a}$ is hydrogen or protected hydroxy; or b) $X^{2a}$ taken together with $X^{3a}$ is methylenedioxy or ethylenedioxy, and $X^1$ and is hydrogen or a pharmaceutically acceptable salt thereof provided that:

i) at least one of $R^{1a}$ through $R^{4a}$ is other than hydrogen;

ii) when $R^{1a}$ is methoxy, $R^{2a}$ is protected hydroxy or methoxy and $R^{3a}$ is methoxy or hydrogen;

iii) when $R^{2a}$ is protected hydroxy, methoxy or protected amino, $R^{3a}$ is hydrogen, hydroxy or methoxy, and $R^4$ is hydrogen;

iv) when $R^{4a}$ is protected hydroxy or protected amino, $R^1$ $R^3$ are hydrogen and $R^2$ is protected hydroxy or protected amino; and v) when $R^1$ is fluoro, chloro, iodo or protected amino, $R^2$ is hydrogen, hydroxy or methoxy, $R^3$ is hydrogen, protected hydroxy or methoxy and $R^4$ is hydrogen.

are within the scope of the present invention. Particular protected hydroxy functions include alkoxy, aryloxy, alkylaryloxy, alkoxyaryloxy and alkoxyalkoxy, e.g., —O—CH$_2$—O—CH$_3$, —O—CH$_2$C$_6$H$_5$ and —O—CO—C$_2$H$_5$. As used herein "alkyl" means C$_{1-6}$ alkyl, "alkoxy" means C$_{1-6}$ alkoxy and "aryl" means phenyl, alkyl substituted phenyl or alkoxy substituted phenyl. Particular protected amino functions are —NHalkanoyl, e.g., —NHCOCH$_3$ and —NHCOOCH$_3$.

Specific compounds of formula (IA) are:

| Compound/ Example Number | Compound Name |
|---|---|
| 14a. | 7-methoxy-8-methoxymethoxy-10H-1,3-dioxolo[4,5-g]indeno[1,2-b]quinoline |
| 15a. | 7,8 dimethoxymethoxy-10H-1,3-dixolo[4,5-g]indeno[1,2-b]quinoline |
| 16a. | 8-methoxymethoxy-10H-1,3-dioxolo[4,5-g]indeno[1,2-b]quinoline |
| 18a. | 2,3-dimethoxy-11H-indeno-8-(4-methoxybenzoxy)-[1,2-b]quinoline |
| 19a. | 2,3-dimethoxy-11H-indeno-7-(4-methoxybenzoxy)-8-methoxy-[1,2-b]quinoline |
| 20a. | 2,3-dibenzoxy-11H-indeno-8-(4-methoxybenzoxy)-[1,2-b]quinoline |
| 21a. | 2-benzoxy-3-methoxy-11H-indeno-8-(4-methoxybenzoxy)-[1,2-b]quinoline |
| 22a. | 2-methoxy-3-benzoxy-11H-indeno-8-(4-methoxybenzoxy)-[1,2-b]quinoline |
| 23a. | 2-methoxy-11H-indeno-8-(4-methoxybenzoxy)-[1,2-b]quinoline |
| 24a. | 2-benzoxy-11H-indeno-8-(4-methoxybenzoxy)-[1,2-b]quinoline |
| 25a. | 7,8-dimethoxybenzofuro-2-(4-methoxybenzyl)-[3,2-b]quinoline |
| 28a. | 6,8-dimethoxymethoxybenzofuro-1,3-dioxolo[3,2-b]quinoline |
| 29a. | 6,8-dibenzoxybenzofuro-2-(4-methoxybenzoxy)-[3,2-b]quinoline |

The data from the Cleavable Complex Assay in Table A, below, shows the relative topoisomerase Types I and II inhibitory activity of the compounds of Formula (I). This assay performed according to the method described in Hsiang, Y. et al., *J. Biol. Chem.*, 260:14873-14878 (1985), correlates well with in vivo anti-tumor activity of topoisomerase inhibitors in animal models of cancer, e.g., camptothecin and its analogs. See Hsiang et al., *Cancer Research*, 49:4385-4389 (1989) and Jaxel et al., *Cancer Research*, 49:1465-1469 (1989). In this assay compounds exhibiting no observable inhibitory activity at concentrations of greater than about 60 μg/mL (indicated by "—" in table A, below) are considered to be of no practical value as topoisomerase inhibitors. Those compounds which exhibit observable activity in the concentration range of from about 12 μg/mL to about 60 μg/mL ("+" in table A) are considered weakly active to moderately active, while those active in the range of from about 3 μg/mL to about 12 μg/mL ("++" in table A) are moderately active. Compounds active at concentrations less than 3 μg/mL ("+++" in table A) are considered strongly active topoisomerase inhibitors. Certain compounds of formula (I), e.g., compounds 1 and 10, inhibit both Type I and Type II topoisomerase.

TABLE A

| Topoisomerase Inhibitory Activity of Compounds of Formula (I) in the Cleavable Complex Assay | | |
|---|---|---|
| Compound Number | Topo I | Topo II |
| 1 | +++ | ++ |
| 2 | + | — |
| 3 | +++ | +++ |
| 4 | — | + |
| 5 | ++ | ++ |
| 6 | — | ++ |
| 7 | — | +++ |
| 8a | ++ | — |
| 8b | +++ | ++ |
| 9 | — | +++ |
| 10 | +++ | + |
| 11 | — | +++ |
| 12 | + | — |
| 13 | — | +++ |
| 14b | +++ | +++ |
| 15b | +++ | +++ |
| 16b | — | + |
| 17 | +++ | — |
| 18 | +++ | ++ |
| 19 | ++ | — |
| 20 | +++ | +++ |
| 21 | +++ | +++ |
| 22 | +++ | +++ |
| 23 | — | + |
| 24 | ++ | ++ |

TABLE A-continued

Topoisomerase Inhibitory Activity of
Compounds of Formula (I) in the Cleavable Complex Assay

| Compound Number | Topo I | Topo II |
| --- | --- | --- |
| 25 | +++ | ++ |
| 26 | ++ | ++ |
| 27 | +++ | ++ |
| 28 | – | + |
| 29 | ++ | ++ |

−Indicates no activity of practical value.
+Indicates positive activity, and the number of + signs indicates relative activity (see description of this assay, above).

In view of such activity, the compounds of formula (I) are active against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, etc. Herein the terms "tumor", "cancer" and "cancerous growths" are used synonymously.

The amount of compound of formula (I) required to be effective as an antitumor agent will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective antitumor dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 75 to about 7500 mg per day, and a typical dose would be about 800 mg per day. If discrete multiple doses are indicated, treatment might typically be 200 mg of a compound of formula (I) given 4 times per day.

Formulations of the present invention, for medical use, comprise an active compound, i.e., a compound of formula (I), together with an acceptable carrier therefor and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal or vaginal administration may be presented as a suppository with a conventional carrier, e.g., cocoa butter or Witepsol S55 (trademark of Dynamite Nobel Chemical, Germany, for a suppository base).

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter. Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*.

EXAMPLE 1

8-Methoxy-10H-1,3-dioxolo[4,5-g]indeno[1,2-b]quinoline (Compound 1)

To 5-methoxyindan-1-one (350 mg, 2 mmol) is added 6[[(4-methylphenyl)imino]methyl]-1,3-benzodioxol-5-amine (512 mg, 1 mmol) in ethanol (4 mL) and 2N sodium hydroxide (1 mL). The reaction mixture is heated at reflux (about 100° C.) for 16 hrs. Upon cooling the reaction product is dissolved in methylene chloride (200 mL) and extracted with a saturated sodium chloride solution (200 mL). The organic layer is dried with a rotatory evaporator. The resulting residue is chromatographed on silica gel with 2:3 ethyl acetate/hexanes to yield 8-Methoxy-10H-1,3-dioxolo[4,5-g]indeno[1,2-b]quinoline (393 mg, 67.4% of theory).

1H-300 NMR (CDCl3): δ3.93 (s, 3H); 3.97 (s, 2H); 6.14 (s, 2H); 7.16–7.05 (m, 3H); 7.50 (s, 1H); 7.99 (s, 1H); 8.15 (d, 1H).

High Resolution Exact Mass: (for $C_{18}H_{13}NO_3$): Calc.=292.0974. Found=292.0983.

EXAMPLE 2

7,8,9-Trimethoxy-10H-1,3-dioxolo[4,5-g]indeno[1,2-b]quinoline (Compound 2)

Using the procedure of Example 1, 4,5,6-trimethoxyindan-1-one (1.10 mg, 4.8 mmol) is reacted with 6[[(4-methylphenyl)imino]methyl]-1,3-benzodioxol-5-amine (1.22 g, 4.8 mmol) to yields 7,8,9-trimethoxy-10H-1,3-dioxolo[4,5-g]indeno[1,2-b]quinoline (0.84 mg, 49.9% of theory).

1H-300 NMR (CDCl3): δ3.94 (s, 2H); 3.99 (s, 3H); 4.06 (s, 3H); 4.09 (s, 3H); 6.15 (s, 3H); 7.12 (s, 1H); 7.56 (s, 1H); 7.56 (s, 1H); 8.03 (s, 1H).

| Elemental analysis: (for $C_{20}H_{17}NO_5$) | | | |
|---|---|---|---|
| | % C | % H | % N |
| Found: | 68.22 | 4.87 | 4.09 |
| Calculated: | 68.37 | 4.88 | 3.99 |

EXAMPLE 3

7,8-Dimethoxy-10H-1,3-dioxolo[4,5-g]indeno[1,2-quinoline (Compound 3)

Using the procedure of Example 1, 5,6-dimethoxyindan-1-one (192 mg, 1 mmol) is reacted with 6[[(4-methylphenyl)imino]methyl]-1,3-benzodioxol-5-amine (255 mg, 1 mmol) to yields 7,8-dimethoxy-10H-1,3-dioxolo[4,5-g]indeno[1,2-b]quinoline (260 mg, 81% of theory).

1H-300 NMR (CDCl3): δ3.92 (s, 2H); 4.02 (s, 3H); 4.09 (s, 3H); 6.14 (s, 2H); 7.11 (s, 1H); 7.14 (s, 1H); 7.51 (s, 1H); 7.73 (s, 1H); 8.00 (s, 1H).

High Resolution Exact Mass: (for $C_{19}H_{15}NO_4$): Calc.=322.1079. Found=322.1094.

EXAMPLE 4

7-Methoxy-10H-1,3-dioxolo[4,5-g]indeno[1,2-g]quinoline (Compound 4)

Using the procedure of Example 1, 6-methoxyindan-1-one (162 mg, 1 mmol) is reacted with 6[[(4-methylphenyl)imino]methyl]-1,3-benzodioxol-5-amine (255 mg, 1 mmol) to yields 7-methoxy-10H-1,3-dioxolo[4,5-g]indeno[1,2-b]quinoline (130 mg, 44.6% of theory).

1H-300 NMR (CDCl3): δ3.94 (s, 2H); 4.00 (s, 3H); 6.15 (s, 2H); 7.07 (dd, J=8.3, 2.6 hz, 1H); 7.13 (s, 1H); 7.51 (d, J=8.3 hz, 1H); 7.54 (s, 1H); 7.76 (d, J=2.44 hz, 1H); 8.05 (s, 1H).

High Resolution Exact Mass: (for $C_{18}H_{13}NO_3$): Calc.=292.0974. Found=292.0998.

EXAMPLE 5

7,9-Dimethoxy-8-hydroxy-10H-1,3-dioxolo[4,5-g]indeno[1,2-b]quinoline (Compound 5)

(A) Using the procedure of Example 1, 4,6-dimethoxy-5-methoxymethoxyindan-1-one (100 mg, 0.4 mmol) is reacted with 6[[(4-methylphenyl)imino]methyl]-1,3-benzodioxol-5-amine (101 mg, 0.4 mmol) to yields 7,9-dimethoxy-8-methoxymethoxy-10H-1,3-dioxolo[4,5-g]indeno[1,2-b]quinoline (120 mg, 79% of theory). This material was used directly in part (B).

(B) The product of part (A) (120 mg, 0.31 mmol), tetrahydrofuran (5 mL) and 2N HCl (5 mL) are heated at reflux (about 80° C.) for about 16 Hrs. After cooling to room temperature, the reaction mixture is washed with about 50 mL saturated aqueous sodium bicarbonate and the organic layer separated and dried over anhydrous magnesium sulfate. The anhydrous magnesium sulfate is removed by filtration and the organic solution is concentrated on a rotary evaporator to a thick residue. This residue is chromatographed (silica gel eluded with 70% ethyl acetate/30% hexane) to yield 7,9-Dimethoxy-8-hydroxy-10H-1,3-dioxolo[4,5-g]indeno[1,2-b]quinoline (41 mg, 39% of theory).

1H-300 MNR (CDCl3): δ3.98 (s, 2H); 4.09 (s, 3H); 4.11 (s, 3H); 5.91 (s, 1H); 6.14 (s, 2H); 7.12 (s, 1H); 7.50 (s, 1H); 7.55 (s, 1H); 8.02 (s, 1H).

High Resolution Exact Mass: (for $C_{19}H_{13}NO_4$): Calc.=388.1029. Found=388.1034.

EXAMPLE 6

6,7-(1,4-Dioxano)-10H-1,3-dioxolo[4,5-g]indeno[1,2-b]quinoline (compound 6)

Using the procedure of Example 1, 6,7-(1,4-dioxano)indan-1-one (115 mg, 0.61 mmol) is reacted with 6[[(4-methylphenyl)mino]methyl]-1,3-benzodioxol-5-amine (154 mg, 0.61 mmol) to yields 6,7-(1,4-dioxano)-10H-1,3-dioxolo[4,5-g]indeno[1,2-b]quinoline (89 mg, 46% of theory).

1H-300 NMR (CDCl3): δ3.95 (s, 2H); 4.42 (m, 2H); 4.63 (m, 2H); 6.14 (s, 2H); 7.01 (d, 1H); 7.08 (d, 1H); 7.09 (s, 1H); 7.59 (s, 1H); 8.02 (s, 1H).

High Resolution Exact Mass: (for $C_{19}H_{13}NO_4$): Calc.=320.0923. Found=320.0947.

EXAMPLE 7

7,8(1,4-Dioxano)-10H-1,3-dioxolo[4,5-g]indeno[1,2-b]quinoline (Compound 7

Using the procedure of Example 1, 5,6-(1,4-dioxano)indan-1-one (191 mg, 1 mmol) is reacted with 6[[(4-methylphenyl)imino]methyl]-1,3-benzodioxol-5-amine (254 mg, 1 mmol) to yields 7,8-(1,4-dioxano)-10H-1,3-dioxolo[4,5-g]indeno[1,2-b]quinoline (205 mg, 64% of theory).

¹H-300 NMR (CDCl₃): δ3.89 (s, 2H); 4.36 (s, 4H); 6.14 (s, 2H); 7.09 (s, 2H); 7.50 (s, 1H); 7.73 (s, 1H); 7.98 (s, 1H).

High Resolution Exact Mass: (for C₁₉H₁₃NO₄): Calc.=320.0923. Found=320.0916.

EXAMPLE 8

7-Hydroxy-8-methoxy-10H-1,3-dioxolo[4,5-g]indeno[1,2-b]quinoline (Compound 8)

(A) Using the procedure of Example 1,5-methoxy-6-methoxymethoxyindan-1-one (452 mg, 2.03 mmol) is reacted with 6[[(4-methylphenyl)imino]methyl]-1,3-benzodioxol-5-amine (517 mg, 2.03 mmol) to yields 7-methoxymethoxy-8-methoxy-10H-1,3-dioxolo[4,5-g]indeno[1,2-b]quinoline. This material is used directly in part (B) without further isolation or purification except for the few miligrams need for NMR and mass spectral studies.

¹H-300 NMR (acetone ⁶D): δ3.76 (s, 3H); 4.14 (s, 2H); 4.16 (s, 3H); 5.54 (s, 2H); 6.40 (s, 2H); 7.44 (s, 1H); 7.51 (s, 1H); 7.58 (s, 1H); 8.30 (s, 1H); 8.33 (s, 1H).

Nominal Mass: m+1=352.

(B) The product of part (A), tetrahydrofuran (10 mL) and 2N HCl (10 mL) are heated at reflux (about 80° C.) for about 16 Hrs. After cooling to room temperature, the reation mixture is washed with about 50 mL saturated aqueous sodium bicarbonate and the organic layer separated and dried over anhydrous magnesium sulfate. The anhydrous magnesium sulfate is removed by filtration and the organic solution is concentrated on a rotory evaporator to a thick residue. This residue is chromatographed (silica gel eluded with 70% ethyl acetate/30% hexane) to yield 7-hydroxy-8-methoxy-10H-1,3-dioxolo[4,5-g]indeno[1,2-b]quinoline (41 mg, 39% of theory).

¹H-300 NMR (d⁶ DMSO): δ3.97 (s, 5H); 6.29 (s, 2H); 7.32 (s, 1H); 7.43 (s, 1H); 7.48 (s, 1H); 7.49 (s, 1H); 8.24 (s, 1H); 9.36 (s, 1H).

High Resolution Exact Mass: (for C₁₈H₁₃NO₄): Calc.=308.0923. Found=308.0933.

EXAMPLE 9

7-(2-Aminopropoxy)-8-methoxy-10H-1,3-dioxolo[4,5-g]indeno[1,2-b]quinoline (Compound 9)

(A) Using the procedure of Example 1, 6-(3-N-phthalimidopropoxy)-8-methoxyindan-1-one (366 mg, 1 mmol) is reacted with 6[[(4-methylphenyl)imino]methyl]-1,3-benzodioxol-5-amine (255 mg, 1 mmol) to yields 7-(3-N-phthalimidopropoxy)-8-methoxy-10H-1,3-dioxolo[4,5-g]indeno[1,2-b]quinoline (268 mg, 54.2% of theory).

¹H-300 NMR (CDCl₃): δ2.35 (m, 2H); 3.83 (s, 3H); 3.89 (s, 2H); 4.01 (t, J=6.83 hz, 2H); 4.31 (t, J=6.23 hz, 2H); 6.14 (s, 2H); 7.07 (s, 1H); 7.10 (s, 1H); 7.49 (s, 1H); 7.69 (s, 1H); 7.73 (d, J=5.37 hz, 1H); 7.75 (d, J=5.62 hz, 1H); 7.87 (d, J=5.62 hz, 1H); 7.89 (d, J=5.37 hz, 1H); 7.98 (s, 1H).

Nominal Mass: m+1=495.

(B) The product of part (A) (50 mg, 0.1 mmol), andydrous ethanol (5 mL) and anhydrous hydrazine (0.2 mL) are heated at about 50° C. under nitrogen for about 16 Hrs. The reaction is then cooled to about 0° C., filtered and the residue washed with anhydrous ethanol (at about 0° C.). The residue is triturated with minimal methylene chloride. To the resulting methylene chloride solution is added hexane until a solid is precipitated. This solid is recovered by filtration and dried, in vacuo, at ambient temperature to yield 7-(2-aminopropoxy)-8-methoxy-10H-1,3-dioxolo[4,5-g]indeno[1,2-b]quinoline (28.9 mg, 79.4% of theory).

¹H-300 NMR (CDCL₃): δ2.10 (m, 2H); 3.01 (t, J=6.72 hz, 2H); 3.91 (s, 2H); 3.99 (s, 3H); 4.32 (t, J=6.35 hz, 2H); 6.14 (s, 2H); 7.11 (s, 1H); 7.13 (s, 1H); 7.50 (s, 1H); 7.75 (s, 1H); 7.99 (s, 1H).

High Resolution Exact Mass: (for C₂₁H₂₀N₂O₄): Calc.=365.1501. Found=365.1486.

EXAMPLE 10

7-(2-Hydroxyethoxy)-8-methoxy-10H-1,3-dioxolo[4,5-g]indeno[1,2-b]quinoline (Compound 10)

Using the procedure of Example 1, 5-methoxy-6-(2-hydroxyethoxy)indan-1-one (222 mg, 1 mmol) is reacted with 6[[(4-methylphenyl)imino]methyl]-1,3-benzodioxol-5-amine (255 mg, 1 mmol) to yields 7-(2-hydroxyethoxy)-8-methoxy-10H-1,3-dioxolo[4,5-g]indeno[1,2-b]quinoline (239 mg, 68% of theory).

¹H-300 NMR (CDCl₃): δ2.61 (t, J=5.85 hz, 1H); 3.93 (s, 2H); 4.00 (s, 3H); 4.05 (m, 2H); 4.34 (t, J=4.64 hz, 2H); 6.14 (s, 2H); 7.11 (s, 1H); 7.15 (s, 1H); 7.50 (s, 1H); 7.78 (s, 1H); 8.00 (s, 1H).

High Resolution Exact Mass: (for C₂₀H₁₇NO₅): Calc.=352.1185. Found=352.1195.

EXAMPLE 11

8-Methoxy-9-hydroxy-10H-1,3-dioxolo[4,5-g]indeno[1,2-b]quinoline (Compound 11)

(A) Using the procedure of Example 1, 4-benzoxy-5-methoxyindan-1-one (mg, 2 mmol) is reacted with 6[[(4-methylphenyl)imino]methyl]-1,3-benzodioxol-5-amine (510 mg, 2 mmol) to yields 8-methoxy-9-hydroxy-10H-1,3-dioxolo[4,5-g]indeno[1,2-b]quinoline (308 mg, 38.7% of theory) which is used as a starting material for part (B).

(B) The product of part (A) (302 mg, 0.76 mmol), anhydrous ethyl acetate (30 mL), anhydrous tetrahydrofuran (8 mL) and 10% palladium on carbon (0.35 g) are shaken in a sealed bottle containing hydrogen at 1 atm. at ambient temperature for about 2 hrs. The reaction is then filtered through a pad of diatomaceous earth filter aid. The solvent is removed by reduced pressure evaporation to yield a solid residue. This residue is dissolved in minimal methylene chloride and hexane is added to precipitate 8-methoxy-9-hydroxy-10H-1,3-dioxolo[4,5-g]indeno[1,2-b]quinoline (220 mg, 94% of theory).

¹H-300 NMR (CDCl₃): δ3.98 (s, 2H); 4.01 (s, 3H); 5.95 (s, 1H); 6.14 (s, 2H); 7.06 (d, 7=8.06 hz, 1H); 7.11 (s, 1H); 7.51 (s, 1H); 7.78 (d, j=8.3 hz, 1H); 8.04 (s, 1H).

High Resolution Exact Mass: (for C₁₈H₁₃NO₄): Calc.=308.0923. Found=308.0945.

EXAMPLE 12

(+/−)7-[2(5H)-3,4-Dihydro-3-oxyfuranone]-8-methoxy-10H-1,3-dioxolo[4,5-g]indeno[1,2-b]quinoline (Compound 12)

Using the procedure of Example 1, 5-methoxy-6-[2(5H)-3,4-dihydro-3-oxyfuranone]indan-1-one (262 mg, 1 mmol) is reacted with 6[[(4-methylphenyl)imino]methyl]-1,3-benzodioxol-5-amine (255 mg, mmol) to yields (+/−)7-[2(5H)-3,4-dihydro-3-oxyfuranone]-

10H-1,3-dioxolo[4,5-g]indeno[1,2-b]quinoline (106 mg, 27% of theory).

$^1$H-300 NMR (CDCl$_3$): δ2.61 (m, 1H); 2.86 (m, 1H); 3.93 (s, 2H); 4.00 (s, 3H); 4.41 (m, 1H); 4.61 (m, 1H); 5.19 (t, j=8.06 hz, 1H); 6.14 (s, 2H); 7.10 (s, 1H); 7.17 (s, 1H); 7.48 (s, 1H); 7.85 (s, 1H); 8.00 (s, 1H).

High Resolution Exact Mass: (for C$_{22}$H$_{17}$NO$_7$): Calc.=392.1134. Found=392.1151.

EXAMPLE 13

7-n-Methylcarbamoyl-8-methoxy-10H-1,3-dioxolo[4,5-g]indeno[1,2-b]quinoline (Compound 13)

Compound 8, prepared in Example 8, (308 mg, 1 mmol), anhydrous methylene chloride (5 mL), 4-dimethylamino pyridine (489 mg, 4 mmol) and methyl isocyanate (171 mg, 0.18 mmol) are stirred at about 0° C. under a dry nitrogen atmosphere for about an hour. The reaction is allowed to cool to ambient temperature. Stirring is continued for about 16 hrs. while maintaining the nitrogen atmosphere. The solvent is then removed by reduced pressure evaporation to give a solid residue. This residue is chromatographed (silica gel eluded with ethyl acetate) to yield 7-n-Methylcarbamoyl-8-methoxy-10H-1,3-dioxolo[4,5-g]indeno[1,2-b]quinoline.

$^1$H-300 NMR (DMSO D$^6$): δ2.26 (s, 3H); 3.62 (s, 5H); 5.94 (s, 2H); 6.97 (s, 1H); 7.09 (s, 1H); 7.14 (s, 1H); 7.15 (s, 1H); 7.89 (s, 1H); 9.00 (s, 1H).

EXAMPLE 14

7-Methoxy-8-methoxymethoxy-10H-1,3-dioxolo[4,5-g]indeno[1,2-b]quinoline (Compound 14a) and
7-Methoxy-8-hydroxy-10H-1,3-dioxolo[4,5-g]indeno[1,2-b]quinoline (Compound 14b)

(A) Using the procedure of Example 1, 5-methoxy-6-methoxymethoxyindan-1-one (1000 mg, 4.5 mmol) is reacted with 6[[(4-methylphenyl)imino]methyl]-1,3-benzodioxol-5-amine (1144 mg, 4.5 mmol) to yields 7-Methoxy-8-methoxymethoxy-10H-1,3-dioxolo[4,5-g]indeno[1,2-b]quinoline (400 mg, 25% of theory).

$^1$H-300 NMR (CDCl$_3$): δ3.53 (s, 3H); 3.84 (s, 2H); 4.01 (s, 3H); 5.29 (s, 2H); 6.07 (s, 2H); 7.04 (s, 1H); 7.35 (s, 1H); 7.44 (s, 1H); 7.69 (s, 1H); 7.94 (s, 1H).

Nominal Mass: m/e=351.

(B) The product of part (A) (80 mg 0.23 mmol) is stirred with trifluoroacetic acid (0.43 mL, 5.6 mmol) and methylene chloride (1 mL) at ambient temperature for about 16 hours. The reaction is then quenched with saturated sodium bicarbonate solution (about 10 mL), and extracted with ethyl acetate (3×10 mL). The combined organic phases are dried over anhydrous sodium sulfate, filtered and stripped of solvent by reduced pressure evaporation to yield 7-methoxy-8-hydroxy-10H-1,3-dioxolo[4,5-g]indeno[1,2-b]quinoline (56 mg, 65% of theory)

$^1$H-300 NMR (CDCl$_3$): δ3.84 (s, 2H); 4.01 (s, 3H); 6.08 (s, 2H); 6.21 (brs, 1H); 7.05 (s, 1H); 7.11 (s, 1H); 7.45 (s,1H); 7.67 (s, 1H); 7.93 (s, 1H).

Nominal Mass: m/e=307.

| Elemental analysis: (for C$_{18}$N$_{13}$N$_1$O$_4$) | | | |
|---|---|---|---|
| | % C | % H | % N |
| Found: | 68.42 | 4.88 | 4.04 |
| Calculated: | 68.37 | 4.88 | 3.99 |

EXAMPLE 15

7,8-Dimethoxymethoxy-10H-1,3-dioxolo[4,5-g]indeno[1,2-b]quinoline (Compound 15a) and
7,8-dihydroxy-10H-1,3-dioxolo[4,5-g]indeno[1,2-b]quinoline (Compound 15b)

(A) Using the procedure of Example 1, 5,6-dimethoxymethoxyindan-1-one (504 mg, 2 mmol) is reacted with 6[[(4-methylphenyl)imino]methyl]-1,3-benzodioxol-5-amine (508 mg, 2 mmol) to yields 7,8-dimethoxymethoxy-10H-1,3-dioxolo[4,5-g]indeno[1,2-b]quinoline (307 mg, 40% of theory).

$^1$H-300 NMR (CDCl$_3$): δ3.53 (s, 3H); 3.54 (s, 3H); 3.85 (s, 2H); 5.30 (s, 2H); 5.35 (s, 2H); 6.07 (s, 2H); 7.03 (s, 1H); 7.35 (s, 1H); 7.43 (s, 1H); 7.92 (s, 2H).

Nominal Mass: m/e=381.

(B) The product of part (A) (307 mg, 0.8 mmol) was hydrolyzed by the procedure of Example 14 (B) using proportionate amounts of the other reagents to yield 7,8-dihydroxy-10H-1,3-dioxolo[4,5-g]indeno[1,2-b]quinoline (6.7 mg, 3% of theory).

$^1$H-300 NMR (d$^6$ DMSO): δ3.81 (s, 2H); 6.18 (s, 2H); 7.00 (s, 1H); 7.34 (s, 1H); 7.36 (s, 1H); 7.39 (s, 1H); 8.14 (s, 1H); 9.31 (brs, 1H); 9.50 (brs, 1H).

Nominal Mass: m/e=293.

EXAMPLE 16

8-Methoxymethoxy-10H-1,3-dioxolo[4,5-g]indeno[1,2-b]quinoline (Compound 16a) and
8-hydroxy-10H-1,3-dioxolo[4,5-g]indeno[1,2-b]quinoline (Compound 16b)

(A) Using the procedure of Example 1, 5-methoxymethoxyindan-1-one (327 mg, 1.7 mmol) is reacted with 6[[(4-methylphenyl)imino]methyl]-1,3-benzodioxol-5-amine (432 mg, 1.7 mmol) to yields 8-methoxymethoxy-10H-1,3-dioxolo[4,5-g]indeno[1,2-b]quinoline (86.3 mg, 15% of theory).

$^1$H-300 NMR (CDCl$_3$): δ3.49 (s, 3H); 3.89 (s, 2H); 5.23 (s, 2H); 6.06 (s, 2H); 7.02 (s, 1H); 7.11 (d, J=8.5 hz, 1H); 7.22 (s, 1H); 7.43 (s, 1H); 7.92 (s, 1H); 7.06 (d, j=8.5 Hz, 1H).

Nominal Mass: m/e=321.

(B) The product of part (A) (25 mg, 0.8 μmol) was hydrolyzed by the procedure of Example 14 (B) using proportionate amounts of the other reagents to yield 8-hydroxy-10H-1,3-dioxolo[4,5-g]indeno[1,2-b]quinoline (5.5 mg, 25% of theory).

$^1$H-300 NMR (d$^6$ DMSO): δ3.91 (s, 2H); 6.17 (s, 2H); 6.85 (d, j=8.0 Hz, 1H); 7.00 (s, 1H); 7.32 (s, 1H); 7.35 (s, 1H); 7.82 (d, j=8.0 Hz, 1H); 8.13 (s, 1H).

Nominal Mass: m/e=277.

EXAMPLES 17-29

The starting materials for Examples 17-29 are the compounds of formula (IIA) and formula (IIIA) where in X$^1$, X$^{2a}$, X$^{3a}$, and R$^{1a}$-R$^{4a}$ are as defined for formula (IA)

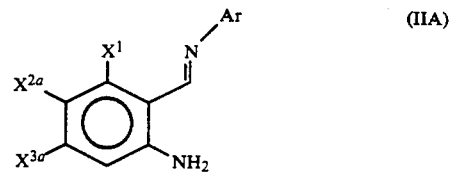
(IIA)

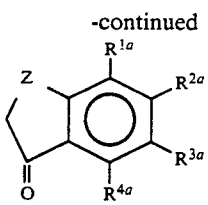

(IIIA)

EXAMPLE 17

2,3-Dimethoxy-11H-indeno-8-chloro-[1,2-b]quinoline (Compound 17)

This compound is prepared by the procedure of Example 1 except that an equivalent amount of the compound of formula (IIIA), wherein Z is $CH_2$; $R^{2a}$ and $R^{3a}$ are methoxy; and $R^{1a}$ and $R^{4a}$ are hydrogen, is used in place of 5-methoxyindan-1-one and an equivalent amount of the compound of formula (IIA) wherein $X^{2a}$ is chloro, and $X^1$ and $X^3$ are hydrogen is used in place of 6[[(4-methylphenyl)imino]methyl]-1,3-benzodioxol-5-amine to yield 2,3-dimethoxy-11H-indeno-8-chloro-[1,2-b]quinoline (24% of theory).

$^1$H-300 NMR (CDCl$_3$): δ3.92 (s, 2H); 3.96 (s, 3H); 4.02 (s, 3H); 7.08 (s, 1H); 7.57 (dd, J=2.2, 9.04 hz 1H); 7.69 (s, 1H); 7.75 (d, J=2.2 hz 1H); 7.99 (s, 1H); 8.04 (d, J=9.04 1H).

Nominal Mass: m/e=311.

EXAMPLE 18

2,3-Dimethoxy-11H-indeno-[1,2-b]quinolin-8-ol (Compound 18)

(A) The same procedure as Example 5 (A) is used except that an equivalent amount of the compound of formula (IIIA), wherein Z is $CH_2$; $R^{2a}$ and $R^{3a}$ are methoxy; and $R^{1a}$ and $R^{4a}$ are hydrogen, is used in place of 4,6-dimethoxy-5-methoxymethoxyindan-1-one and an equivalent amount of the compound of formula (IIA) wherein $X^{2a}$ is 4-methoxybenzoxy, and $X^1$ and $X^3$ are hydrogen is used in place of 6[[(4-methylphenyl)imino]methyl]-1,3-benzodioxol-5-amine to yield 2,3-dimethoxy-11H-indeno-8-(4-methoxybenzoxy)-[1,2-b]quinoline. This material was used directly in part (B).

Nominal Mass: m/e=413.

(B) The procedure of Example 14 (B) is used to remove the hydroxy protecting group, i.e., 4-methoxybenzyl, from the product of part (A) above and to yield 2,3-dimethoxy-11H-indeno-[1,2-b]quinolin-8-ol (88% of theory).

$^1$H-300 NMR (d$^6$DMSO): δ3.85 (s, 3H); 3.89 (s, 3H); 3.92 (s, 2H); 7.14 (d, J=2.69 hz, 1H); 7.23 (dd, J=2.69, 9.03 hz, 1H); 7.27 (s, 1H); 7.52 (s, 1H); 7.87 (d, J=9.03 hz, 1H); 8.12 (s, 1H).

| Elemental analysis: (for C$_{18}$H$_{15}$NO$_3$) | | | |
|---|---|---|---|
| | % C | % H | % N |
| Found: | 73.48 | 5.17 | 4.77 |
| Calculated: | 75.50 | 5.16 | 4.78 |

EXAMPLE 19

2,3-Dimethoxy-11H-indeno-8-methoxy-[1,2-b]quinolin-7-ol (Compound 19)

(A) The same procedure as Example 5 (A) except is used that an equivalent amount of the compound of formula (IIIA), wherein Z is $CH_2$; $R^{2a}$ and $R^{3a}$ are methoxy; and $R^{1a}$ and $R^{4a}$ are hydrogen, is used in place of 4,6-dimethoxy-5-methoxymethoxyindan-1-one and an equivalent amount of the compound of formula (IIA), wherein $X^1$ is hydrogen, $X^{2a}$ is methoxy, and $X^3$ is 4-methoxybenzoxy, is used in place of 6[[(4-methylphenyl)imino]methyl]-1,3-benzodioxol-5-amine to yield 2,3-dimethoxy-11H-indeno-7-(4-methoxybenzoxy)-8-methoxy[1,2-b]quinoline (mp, 216°-218° C.). This material was used directly in part (B).

FAB m+1=444.

(B) The procedure of Example 14 (B) is used to remove the hydroxy protecting group, i.e., 4-methoxybenzyl, from the product of part (A) above and to yield 2,3-dimethoxy-11H-indeno-8-methoxy-[1,2-b]quinolin-7-ol (19% of theory).

$^1$H-300 NMR (CDCl$_3$): δ3.87 (s, 2H); 3.96 (s, 3H); 4.01 (s, 3H); 4.02 (s, 3H); 7.05 (d, J=6.4 hz,2H); 7.61 (s, 1H); 7.72 (s, 1H); 7.95 (s, 1H).

Nominal Mass: m/e=323.

EXAMPLE 20

2,3-Dihydroxy-11H-indeno-[1,2-b]quinolin-8-ol (Compound 20)

(A) The same procedure as Example 5 (A) is used except that an equivalent amount of the compound of formula (IIIA), wherein Z is $CH_2$; $R^{2a}$ and $R^{3a}$ are benzy; and $R^{1a}$ and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 2,3-dibenzoxy-11H-indeno-8-(4-methoxybenzoxy)-[1,2-b]quinoline. This material was used directly in part (B).

Nominal Mass: m/e=473.

(B) The procedure of Example 14 (B) is used to remove the hydroxy protecting groups, i.e., 4-methoxybenzyl and benzyl, from the product of part (A) above and to yield 2,3-dihydroxy-11H-indeno-[1,2-b]quinolin-8-ol (67% of theory).

$^1$H-300 NMR (d$^6$DMSO+D$_2$O): §3.96 (r, 2H); 7.16 (s, 1H); 7.43 (d, J=2.69 hz, 1H); 7.55 (dd, J=2.69, 9.04 hz, 1H); 7.75 (s, 1H); 8.03 (d, J=9.04 hz, 1H); 8.69 (s, 1H).

Nominal Mass: m/e=265.

EXAMPLE 21

2-Hydroxy-3-methoxy-11H-indeno-[1,2-b]quinolin-8-ol (Compound 21)

(A) The same procedure as Example 5 (A) is used except that an equivalent amount of the compound of formula (IIIA), wherein Z is $CH_2$; $R^{2a}$ is benzoxy; $R^{3a}$ is methoxy; and $R^{1a}$ and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 2-benzoxy-3-methoxy-11H-indeno-8-(4-methoxybenzoxy)-[1,2-b]quinoline. This material was used directly in part (B).

Nominal Mass: m/e=443.

(B) The procedure of Example 14 (B) is used to remove the hydroxy protecting groups, i.e., 4-methoxybenzyl and benzyl, from the product of part (A) above and to yield 2-hydroxy-3-methoxy-11H-indeno-[1,2-b]quinolin-8-ol (46% of theory).

Nominal Mass: m/e=279.

EXAMPLE 22

2-Methoxy-3-hydroxy-11H-indeno-[1,2-b]quinolin-8-ol (Compound 22)

(A) The same procedure as Example 5 (A) is used except that an equivalent amount of the compound of formula (IIIA), wherein Z is $CH_2$; $R^{2a}$ is methoxy; $R^{3a}$ is benzoxy; and $R^{1a}$ and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 2-methoxy-3-benzoxy-11H-indeno-8-(4-methoxybenzoxy)-[1,2-b]quinoline. This material was used directly in part (B).

Nominal Mass: m/e=443.

(B) The procedure of Example 14 (B) is used to remove the hydroxy protecting groups, i.e., 4-methoxybenzyl and benzyl, from the product of part (A) above and to yield 2-methoxy-3-hydroxy-11H-indeno-[1,2-b]quinolin-8-ol (% of theory).

High Resolution Exact Mass: (for $C_{17}H_{13}NO_3$): Calc.=280.0974. Found=280.0963.

EXAMPLE 23

2-Methoxy-11H-indeno-[1,2-b]quinolin-8-ol (Compound 23)

(A) The same procedure as Example 5 (A) is used except that an equivalent amount of the compound of formula (IIIA), wherein Z is $CH_2$; $R^{2a}$ is methoxy; and $R^{1a}$, $R^{3a}$, and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 2-methoxy-11H-indeno-8-(4-methoxybenzoxy)-[1,2-b]quinoline. This material was used directly in part (B).

Nominal Mass: m/e=383.

B) The procedure of Example 14 (B) is used to remove the hydroxy protecting group, i.e., 4-methoxybenzyl, from the product of part (A) above and to yield 2-methoxy-11H-indeno-[1,2-b]quinolin-8-ol.

High Resolution Exact Mass: (for $C_{17}H_{13}NO_2$): Calc.=264.1025. Found=264.1036.

EXAMPLE 24

2-Hydroxy-11H-indeno-[1,2-b]quinolin-8-ol (Compound 24)

(A) The same procedure as Example 5 (A) is used except that an equivalent amount of the compound of formula (IIIA), wherein Z is $CH_2$; $R^{2a}$ is benzoxy; and $R^{1a}$, $R^{3a}$, and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 2-benzoxy-11H-indeno-8-(4-methoxybenzoxy)-[1,2-b]quinoline. This material was used directly in part (B).

Nominal Mass: m/e=459.

(B) The procedure of Example 14 (B) is used to remove the hydroxy protecting groups, i.e., 4-methoxybenzyl and benzyl, from the product of part (A) above and to yield 2-hydroxy-11H-indeno-[1,2-b]quinolin-8-ol.

Nominal Mass: m/e=249.

EXAMPLE 25

7,8-Dimethoxybenzofuro[3,2-b]quinolin-2-ol (Compound 25)

(A) The same procedure as Example 5 (A) is used except that an equivalent amount of the compound of formula (IIIA), wherein Z is O; $R^{2a}$ and $R^{3a}$ are methoxy; and $R^{1a}$ and $R^{4a}$ are hydrogen, is used in place of 4,6-dimethoxy-5-methoxymethoxyindan-1-one and an equivalent amount of the compound of formula (IIA), wherein $X^1$ and $X^3$ are hydrogen and $X^{2a}$ is 4-methoxybenzoxy, is used in place of 6[[(4-methylphenyl)imino]methyl]-1,3-benzodioxol-5-amine to yield 7,8-dimethoxybenzofuro-2-(4-methoxybenzyl)-[3,2-b]quinoline. This material was used directly in part (B).

(B) The procedure of Example 14 (B) is used to remove the hydroxy protecting group, i.e., 4-methoxybenzyl, from the produce of part (A) above and to yield 7,8-dimethoxybenzofuro[3,2-b]quinolin-2-ol (67% of theory).

$^1$H-300 NMR ($d^6$ DMSO): δ3.65 (s, 6H); 7.06 (m, 2H); 7.17 (s, 1H); 7.4 (s, 1H); 7.73 (d, J=8.5 hz 1H); 8.01 (s, 1H); 9.74 (s, 1H)

High Resolution Exact Mass: (for $C_{17}H_{13}NO_4$): Calc.=296.0923. Found=296.0926.

EXAMPLE 26

7,8-Dimethoxybenzofuro-1,3-dioxolo[3,2-b]quinoline (Compound 26)

This compound is prepared by the procedure of Example 1 except that an equivalent amount of the compound of formula (IIIA), wherein Z is O; $R^{2a}$ and $R^{3a}$ are methoxy; and $R^{1a}$ and $R^{4a}$ are hydrogen, is used in place of 5-methoxyindan-1-one and an equivalent amount of the compound of formula (IIA) wherein $X^{2a}$ together with $X^{3a}$ is methylenedioxy and $X^1$ is hydrogen is used in place of 6[[(4-methylphenyl)imino]methyl]-1,3-benzodioxol-5-amine to yield 7,8-dimethoxybenzofuro-1,3-dioxolo[3,2-b]quinoline (47% of theory).

$^1$H-300 NMR (CDCl$_3$): δ4.02 (s, 6H); 6.12 (s, 2H); 7.09 (s, 1H); 7.15 (s, 1H); 7.53 (s, 1H); 7.72 (s, 1H); 7.93 (s, 1H).

EXAMPLE 27

8-Methoxybenzofuro-1,3-dioxolo[3,2-b]quinoline (Compound 27)

This compound is prepared by the procedure of Example 1 except that an equivalent amount of the compound of formula (IIIA), wherein Z is O; $R^{2a}$ is methoxy; and $R^{1a}$, $R^{3a}$ and $R^{4a}$ are hydrogen, is used in place of 5-methoxyindan-1-one and an equivalent amount of the compound of formula (IIA) wherein $X^{2a}$ together with $X^{3a}$ is methylenedioxy and $X^1$ is hydrogen is used in place of 6[[(4-methylphenyl)imino]methyl]-1,3-benzodioxol-5-amine to yield 7,8-dimethoxybenzofuro-1,3-dioxolo[3,2-b]quinoline (7.8% of theory).

$^1$H-300 NMR (CDCl$_3$): δ3.9 (s, 3H); 6.22 (s, 2H); 7.06 (dd, 1H); 7.36 (d, 1H); 7.44 (s, 1H); 7.48 (s, 1H); 8.07 (d, 1H); 8.33 (s, 1H).

Nominal Mass: m/e=293.

EXAMPLE 28

6,8-Dihydroxybenzofuro-1,3-dioxolo[3,2-b]quinoline (Compound 28)

(A) The same procedure as Example 5 (A) is used except that an equivalent amount of the compound of formula (IIIA), wherein Z is O; $R^{2a}$ and $R^{4a}$ are methoxymethoxy; and $R^{1a}$ and $R^{3a}$ are hydrogen, is used in place of 4,6-dimethoxy-5-methoxymethoxyindan-1-one and an equivalent amount of the compound of formula (IIA), wherein $X^{2a}$ together with $X^{3a}$ is methylenedioxy and $X^1$ is hydrogen, is used in place of 6[[(4-methylphenyl)imino]methyl]-1,3-benzodioxol-5-amine to yield 6,8-dimethoxymethoxybenzofuro-1,3-dioxolo[3,2-b]quinoline.

$^1$H-300 NMR (CDCl$_3$): δ2.50 (s, 3H); 2.65 (s, 3H); 5.30 (s, 2H); 5.65 (s, 2H); 6.15 (s, 2H); 6.85 (s, 1H); 6.98 (s, 1H); 7.19 (s, 1H); 7.28 (s, 1H); 8.05 (s, 1H).

This material was used directly in part (B).

(B) The procedure of Example 14 (B) is used to remove the hydroxy protecting group, i.e., 4-methoxybenzyl, from the product of part (A) above and to yield 6,8-dihydroxybenzofuro-1,3-dioxolo[3,2-b]quinoline (9.8% of theory).

$^1$H-NMR(d$_6$ DMSO) δ6.20 (s, 2H); 6.35 (s, 1H); 6.48 (s, 1H); 7.4 (s, 1H); 7.42 (s, 1H); 8.15 (s, 1H); 10.15 (broad singlet, 1H, OH).

Nominal Mass: m/e=295.

EXAMPLE 29

6,8-Dihydroxybenzofuro[3,2-b]quinolin-2-ol (Compound 29)

(A) The same procedure as Example 5 (A) is used except that an equivalent amount of the compound of formula (IIIA), wherein Z is O; $R^{2a}$ and $R^{4a}$ are benzoxy; and $R^{1a}$ and $R^{3a}$ are hydrogen, is used in place of 4,6-dimethoxy-5-methoxymethoxyindan-1-one and an equivalent amount of the compound of formula (IIA), wherein $X^{2a}$ is 4-methoxybenzoxy $X^1$ and $X^{3a}$ are hydrogen, is used in place of 6[[(4-methylphenyl)imino]methyl]-1,3-benzodioxol-5-amine to yield 6,8-dibenzoxybenzofuro-2-(4-methoxybenzoxy)-[3,2-b]quinoline.

This material was used directly in part (B).

(B) The procedure of Example 14 (B) is used to remove the hydroxy protecting group, i.e., 4-methoxybenzyl, from the product of part (A) above and to yield 6,8-dihydroxybenzofuro[3,2-b]quinolin-2-ol (1.4% of theory).

$^1$H-300 NMR (d$^6$ DMSO): δ5.22 (s, 2H); 5.50 (s, 2H); 6.76 (s, 1H); 7.06 (s, 1H); 7.23-7.53 (m, 11H); 7.64 (s, 1H); 7.67 (s, 1H); 7.98 (d, 1H); 8.22 (s, 1H).

| Elemental analysis: (for C$_{29}$H$_{21}$NO$_4$) | | | |
|---|---|---|---|
| | % C | % H | % N |
| Found: | 76.45 | 4.87 | 3.03 |
| Calculated: | 77.84 | 4.73 | 3.13 |

EXAMPLES 30-38

In a manner similar to the above Examples, and as described in the specification above, the following compounds of formula (I) can be prepared:

Formula (I)

| Example | X$^1$ | X$^2$ | X$^3$ | Z | R$^1$ | R$^2$ | R$^3$ | R$^4$ |
|---|---|---|---|---|---|---|---|---|
| 30 | H | O—Me—O | | NH | OCH$_3$ | OH | H | H |
| 31 | H | F | H | NH | H | OCH$_3$ | NH$_2$ | H |
| 32 | H | Cl | OH | HN | Br | OH | OC$_3$H$_6$NH$_2$ | H |
| 33 | H | Br | H | O | Cl | OH | OC$_2$H$_4$NH$_2$ | H |
| 34 | H | I | H | O | I | OH | OC$_3$H$_6$OH | H |
| 35 | H | OCH$_3$ | H | O | NH$_2$ | H | OC$_3$H$_6$NH$_2$ | H |
| 36 | H | OH | H | O | F | OCH$_3$ | OCH$_3$ | H |
| 37 | H | O—Et—O | | CH$_2$ | H | OH | OH | H |
| 38 | H | OH | H | CH$_2$ | H | OH | H | OH |
| 39 | H | O—Et—O | | CH$_2$ | H | O—Et—O | | H |

Me = CH$_2$
Et = C$_2$H$_4$

EXAMPLE 40

Pharmaceutical formulations (A) Transdermal System

| Ingredients | Amount |
|---|---|
| Active compound | 600.0 mg |
| Silicone fluid | 450.0 mg |
| Colloidal silicone dioxide | 25.0 mg |

The silicone fluid and active compound are mixed together and the colloidal silicone dioxide is reacted with to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

(B) Oral Tablet

| Ingredients | Amount |
|---|---|
| Active compound | 200.0 mg |
| Starch | 20.0 mg |
| Magnesium Stearate | 1.0 mg |

The active compound and the starch are granulated with water and dried. Magnesium stearate is added to the dried granules and the mixture is thoroughly blended. The blended mixture is compressed into a tablet.

(C) Suppository

| Ingredients | Amount |
|---|---|
| Active compound | 150.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

(D) Injection

| Ingredients | Amount |
|---|---|
| Active Compound | 20.0 mg |
| Suspending Agnet | q.s. |
| Buffering Agents | q.s. |
| Propylene glycol | 0.4 |
| Water for injection | 0.6 mL |

The active compound and buffering agents are dissolved in the propylene glycol at about 50° C. The water for injection is then added with stirring and the resulting solution is filtered, filled into an ampule, sealed and sterilized by autoclaving.

(E) Capsule

| Ingredients | Amount |
|---|---|
| Active Compound | 200.0 mg |
| Lactose | 450.0 mg |
| Magnesium stearate | 5.0 mg |

The finely ground active compound is mixed with the lactose and stearate and packed into a gelatin capsule.

We claim:

1. A compound of formula (I)

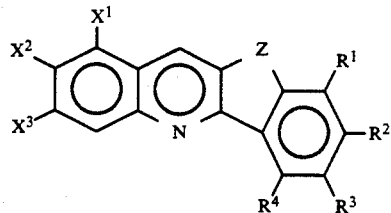

wherein:
$R^1$ is hydrogen, hydroxy, fluoro, chloro, bromo, iodo, methoxy or amino;
$R^2$ is hydrogen, hydroxy, methoxy or amino;
$R^3$ is hydrogen, hydroxy, methoxy, methoxymethoxy, amino, —OCONH$_2$, 2(5H)-3,4-dihydro-3-oxyfuranone, 2-hydroxyethoxy, 2-aminoethoxy, 3-hydroxypropoxy or 3-aminopropoxy; or taken together with $R^2$ or $R^4$, methylenedioxy or ethylenedioxy;
$R^4$ is hydrogen, hydroxy or amino;
Z is —CH$_2$— and
a) $X^1$ is hydrogen; $X^2$ is hydrogen, hydroxy, fluoro, chloro, bromo, iodo or methoxy; and $X^3$ is hydrogen or hydroxy; or
b) $X^2$ taken together with $X^3$ is methylenedioxy or ethylenedioxy, and $X^1$ is hydrogen or a pharmaceutically acceptable salt thereof provided that:
i) at least one of $R^1$ through $R^4$ is other than hydrogen;
ii) when $R^1$ is methoxy, $R^2$ is hydroxy or methoxy, $R^3$ is hydrogen or methoxy and $R^4$ is hydrogen;
iii) when $R^2$ is hydroxy, methoxy or amino, $R^3$ is hydrogen, hydroxy or methoxy; $R^4$ is hydrogen; and $X^2$ and $X^3$ must be other than hydrogen;
iv) when $R^4$ is hydroxy or amino, $R^1$ and $R^3$ are hydrogen and $R^2$ is hydroxy or amino;
v) when $R^1$ is fluoro, chloro, iodo or amino, $R^2$ is hydroxy, methoxy or methoxy, $R^3$ is hydrogen, hydroxy or methoxy and $R^4$ is hydrogen.

2. A compound of claim 1 wherein $X^2$ taken together with $X^3$ is methylenedioxy and Z is —CH$_2$—.

3. A compound of claim 1 wherein $X^2$ is hydroxy, chloro or methoxy; $X^3$ is hydrogen or hydroxy and Z is —CH$_2$—.

4. The compound of claim 1 which is:
8-methoxy-10H-1,3-dioxolo[4,5-g]indeno[1,2-b]quinoline,
7,8,9-trimethoxy-10H-1,3-dioxolo[4,5-g]indeno[1,2-b]quinoline,
7,8-dimethoxy-10H-1,3-dioxolo[4,5-g]indeno[1,2-b]quinoline,
7-methoxy-10H-1,3-dioxolo[4,5-g]indeno[1,2-b]quinoline,
7,9-dimethoxy-8-hydroxy-10H-1,3-dioxolo[4,5-g]indeno[1,2-b]quinoline,
6,7-(1,4-dioxano)-10H-1,3-dioxolo[4,5-g]indeno[1,2-b]quinoline,
7,8-(1,4-dioxano)-10H-1,3-dioxolo[4,5-g]indeno[1,2-b]quinoline,
7-methoxymethoxy-8-methoxy-10H-1,3-dioxolo[4,5-g]indeno[1,2-b]quinoline,
7-hydroxy-8-methoxy-10H-1,3-dioxolo[4,5-g]indeno[1,2-b]quinoline,
7-(2-aminoethoxy)-8-methoxy-10H-1,3-dioxolo[4,5-g]indeno[1,2-b]quinoline,
7-(2-hydroxyethoxy)-8-methoxy-10H-1,3-dioxolo[4,5-g]indeno[1,2-b]quinoline,
8-methoxy-9-hydroxy-10H-1,3-dioxolo[4,5-g]indeno[1,2-b]quinoline,
(+/−)7-[2(5H)-3,4-dihydro-3-oxyfuranone]-8-methoxy-10H-1,3-dioxolo[4,5-g]indeno[1,2-b]quinoline,
7-n-methylcarbamoyl-8-methoxy-10H-1,3-dioxolo[4,5-g]indeno[1,2-b]quinoline
7-methoxy-8-hydroxy-10H-1,3-dioxolo[4,5-g]indeno[1,2-b]quinoline
7,8-dihydroxy-10H-1,3-dioxolo[4,5-g]indeno[1,2-b]quinoline
8-hydroxy-10H-1,3-dioxolo[4,5-g]indeno[1,2-b]quinoline
2,3-dimethoxy-11H-indeno-8-chloro-[1,2-b]quinoline
2,3-dimethoxy-11H-indeno-[1,2-b]quinolin-8-ol or 2,3-dimethoxy-11H-indeno-8-methoxy-[1,2-b]quinolin-7-ol.

5. A pharmaceutical formulation comprising a compound of formula (I),

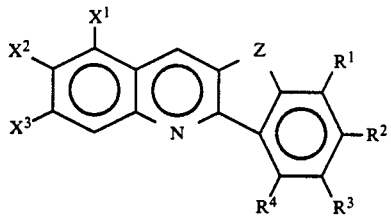

wherein:
R¹ is hydrogen, hydroxy, fluoro, chloro, bromo, iodo, methoxy or amino;
R² is hydrogen, hydroxy, methoxy or amino;
R³ is hydrogen, hydroxy, methoxy, methoxymethoxy, amino, —OCONH₂, [2(5H)-3,4-dihydro-3-oxyfuranone], 2-hydroxyethoxy, 2-aminoethoxy, 3-hydroxypropoxy or 3-aminopropoxy; or taken together with R² or R⁴, methylenedioxy or ethylenedioxy;
R⁴ is hydrogen, hydroxy or amino;
Z is —CH₂—; and
  a) X¹ is hydrogen; X² is hydrogen, hydroxy, fluoro, chloro, bromo, iodo or methoxy; and X³ is hydrogen or hydroxy; or
  b) X² taken together with X³ is methylenedioxy or ethylenedioxy, and X¹ is hydrogen
or a pharmaceutically acceptable salt thereof provided that:
  i) at least one of R¹ through R⁴ is other than hydrogen;
  ii) when R¹ is methoxy, R² is hydroxy or methoxy, R³ is hydrogen or methoxy and R⁴ is hydrogen;
  iii) when R² is hydroxy, methoxy or amino, R³ is hydrogen, hydroxy or methoxy, and R⁴ is hydrogen;
  iv) when R⁴ is hydroxy or amino, R¹ and R³ are hydrogen and R² is hydroxy or amino; and
  v) when R¹ is fluoro, chloro, iodo or amino, R² is hydrogen, hydroxy or methoxy, R³ is hydrogen, hydroxy or methoxy and R⁴ is hydrogen.

6. A formulation of claim 5 wherein for the compound of formula (I) X² taken together with X³ is methylenedioxy and Z is —CH₂—.

7. A formulation of claim 5 wherein for the compound of formula (I) X² is chloro, hydroxy or methoxy; X³ is hydrogen or hydroxy and Z is —CH₂—.

8. A formulation of claim 5 wherein the compound of formula (I) is:
8-methoxy-10H-1,3-dioxolo[4,5-g]indeno[1,2-b]quinoline,
7,8,9-trimethoxy-10H-1,3-dioxolo[4,5-g]indeno[1,2-b]quinoline,
7,8-dimethoxy-10H-1,3-dioxolo[4,5-g]indeno[1,2-b]quinoline,
7-methoxy-10H-1,3-dioxolo[4,5-g]indeno[1,2-b]quinoline,
7,9-dimethoxy-8-hydroxy-10H-1,3-dioxolo[4,5-g]indeno[1,2-b]quinoline,
6,7-(1,4-dioxano)-10H-1,3-dioxolo[4,5-g]indeno[1,2-b]quinoline,
6,7-(1,4-dioxano)-10H-1,3-dioxolo[4,5-g]indeno[1,2-b]quinoline,
7-methoxymethoxy-8-methoxy-10H-1,3-dioxolo[4,5-g]indeno[1,2-b]quinoline,
7-hydroxy-8-methoxy-10H-1,3-dioxolo[4,5-g]indeno[1,2-b]quinoline,
7-(2-aminoethoxy)-8-methoxy-10H-1,3-dioxolo[4,5-g]indeno[1,2-b]quinoline,
7-(2-hydroxyethoxy)-8-methoxy-10H-1,3-dioxolo[4,5-g]indeno[1,2-b]quinoline,
8-methoxy-9-hydroxy-10H-1,3-dioxolo[4,5-g]indeno[1,2-b]quinoline,
(+/−)7-[2(5H)-3,4-dihydro-3-oxyfuranone]-8-methoxy-10H-1,3-dioxolo[4,5-g]indeno[1,2-b]quinoline,
7-n-methylcarbamoyl-8-methoxy-10H-1,3-dioxolo[4,5-g]indeno[1,2-b]quinoline
7-methoxy-8-hydroxy-10H-1,3-dioxolo[4,5-g]indeno[1,2-b]quinoline
7,8-dihydroxy-10H-1,3-dioxolo[4,5-g]indeno[1,2-b]quinoline
8-hydroxy-10H-1,3-dioxolo[4,5-g]indeno[1,2-b]quinoline
2,3-dimethoxy-11H-indeno-8-chloro-[1,2-b]quinoline
2,3-dimethoxy-11H-indeno-[1,2-b]quinolin-8-ol or
2,3-dimethoxy-11H-indeno-8-methoxy-[1,2-b]quinolin-7-ol.

9. A method of inhibiting a topoisomerase enzyme comprising contacting said enzyme with an effective inhibitory amount of a compound of formula (I)

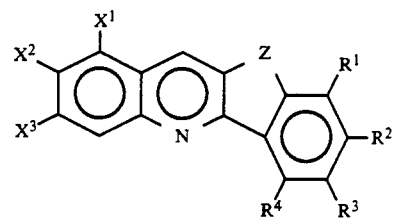

wherein:
R¹ is hydrogen, hydroxy, fluoro, chloro, bromo, iodo, methoxy or amino;
R² is hydrogen, hydroxy, methoxy or amino;
R³ is hydrogen, hydroxy, methoxy, methoxymethoxy, amino, —OCONH₂, [2(5H)-3,4-dihydro-3-oxyfuranone], 2-hydroxyethoxy, 2-aminoethoxy, 3-hydroxypropoxy or 3-aminopropoxy; or taken together with R² or R⁴, methylenedioxy or ethylenedioxy;
R⁴ is hydrogen, hydroxy or amino;
Z is —CH₂—; and
  a) X¹ is hydrogen; X² is hydrogen, hydroxy, fluoro, chloro, bromo, iodo or methoxy; and X³ is hydrogen or hydroxy; or
  b) X² taken together with X³ is methylenedioxy or ethylenedioxy, and X¹ is hydrogen
or a pharmaceutically acceptable salt thereof provided that:
  i) at least one of R¹ through R⁴ is other than hydrogen;
  ii) when R¹ is methoxy, R² is hydroxy or methoxy, R³ is hydrogen or methoxy and R⁴ is hydrogen;
  iii) when R² is hydroxy, methoxy or amino, R³ is hydrogen, hydroxy or methoxy, and R⁴ is hydrogen;
  iv) when R⁴ is hydroxy or amino, R¹ and R³ are hydrogen and R² is hydroxy or amino; and v) when R¹ is fluoro, chloro, iodo or amino, R² is hydrogen, hydroxy or methoxy, R³ is hydrogen, hydroxy or methoxy and R⁴ is hydrogen.

10. A method of claim 9 wherein for the compound of formula (I), X² taken together with X³ is methylenedioxy and Z is —CH₂—.

11. A method of claim 9 wherein for the compound of formula (I), X² is chloro, hydroxy or methoxy; X³ is hydrogen or hydroxy and Z is —CH₂—.

12. The method of claim 9 wherein the compound of Formula (I) is:
8-methoxy-10H-1,3-dioxolo[4,5-g]indeno[1,2-b]quinoline,
7,8,9-trimethoxy-10H-1,3-dioxolo[4,5-g]indeno[1,2-b]quinoline,
7,8-dimethoxy-10H-1,3-dioxolo[4,5-g]indeno[1,2-b]quinoline,
7-methoxy-10H-1,3-dioxolo[4,5-g]indeno[1,2-b]quinoline,
7,9-dimethoxy-8-hydroxy-10H-1,3-dioxolo[4,5-g]indeno[1,2-b]quinoline,
6,7-(1,4-dioxano)-10H-1,3-dioxolo[4,5-g]indeno[1,2-b]quinoline,
6,7-(1,4-dioxano)-10H-1,3-dioxolo[4,5-g]indeno[1,2-b]quinoline,
7-methoxymethoxy-8-methoxy-10H-1,3-dioxolo[4,5-g]indeno[1,2-b]quinoline,
7-hydroxy-8-methoxy-10H-1,3-dioxolo[4,5-g]indeno[1,2-b]quinoline,
7-(2-aminoethoxy)-8-methoxy-10H-1,3-dioxolo[4,5-g]indeno[1,2-b]quinoline,
7-(2-hydroxyethoxy)-8-methoxy-10H-1,3-dioxolo[4,5-g]indeno[1,2-b]quinoline,
8-methoxy-9-hydroxy-10H-1,3-dioxolo[4,5-g]indeno[1,2-b]quinoline,
(+/−)7-[2(5H)-3,4-dihydro-3-oxyfuranone]-8-methoxy-10H-1,3-dioxolo[4,5-g]indeno[1,2-b]quinoline,
7-n-methylcarbamoyl-8-methoxy-10H-1,3-dioxolo[4,5-g]indeno[1,2-b]quinoline
7-methoxy-8-hydroxy-10H-1,3-dioxolo[4,5-g]indeno[1,2-b]quinoline
7,8-dihydroxy-10H-1,3-dioxolo[4,5-g]indeno[1,2-b]quinoline
8-hydroxy-10H-1,3-dioxolo[4,5-g]indeno[1,2-b]quinoline
2,3-dimethoxy-11H-indeno-8-chloro-[1,2-b]quinoline
2,3-dimethoxy-11H-indeno-[1,2-b]quinolin-8-ol or
2,3-dimethoxy-11H-indeno-8-methoxy-[1,2-b]quinolin-7-ol.

13. A method of treating a tumor in a mammal comprising administering to said mammal, an effective antitumor amount of a compound of formula (I)

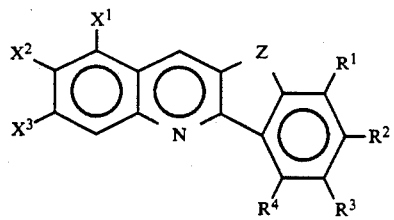

wherein:
R¹ is hydrogen, hydroxy, fluoro, chloro, bromo, iodo, methoxy or amino;
R² is hydrogen, hydroxy, methoxy or amino;
R³ is hydrogen, hydroxy, methoxy, methoxymethoxy, amino, —OCONH₂, [2(5H)-3,4-dihydro-3-oxyfuranone], 2-hydroxyethoxy, 2-aminoethoxy, 3-hydroxypropoxy or 3-aminopropoxy; or taken together with R² or R⁴, methylenedioxy or ethylenedioxy;
R⁴ is hydrogen, hydroxy or amino;
Z is —CH₂—; and
a) X¹ is hydrogen; X² is hydrogen, hydroxy, fluoro, chloro, bromo, iodo or methoxy; and X³ is hydrogen or hydroxy; or
b) X² taken together with X³ is methylenedioxy or ethylenedioxy, and X¹ is hydrogen
or a pharmaceutically acceptable salt thereof provided that:
i) at least one of R¹ through R⁴ is other than hydrogen;
ii) when R¹ is methoxy, R² is hydroxy or methoxy, R³ is hydrogen or methoxy and R⁴ is hydrogen;
iii) when R² is hydroxy, methoxy or amino, R³ is hydrogen, hydroxy or methoxy, and R⁴ is hydrogen;
iv) when R⁴ is hydroxy or amino, R¹ and R³ are hydrogen and R² is hydroxy or amino; and
v) when R¹ is fluoro, chloro, iodo or amino, R² is hydrogen, hydroxy or methoxy, R³ is hydrogen, hydroxy or methoxy and R⁴ is hydrogen.

14. A method of claim 13 wherein for the compound of formula (I) X² taken together with X³ is methylenedioxy and Z is —CH₂—.

15. A method of claim 13 wherein for the compound of formula (I) X² is chloro, hydroxy or methoxy; X³ is hydrogen or hydroxy and Z is —CH₂—.

16. The method of claim 13 wherein the compound of Formula (I) is:
8-methoxy-10H-1,3-dioxolo[4,5-g]indeno[1,2-b]quinoline,
7,8,9-trimethoxy-10H-1,3-dioxolo[4,5-g]indeno[1,2-b]quinoline,
7,8-dimethoxy-10H-1,3-dioxolo[4,5-g]indeno[1,2-b]quinoline,
7-methoxy-10H-1,3-dioxolo[4,5-g]indeno[1,2-b]quinoline,
7,9-dimethoxy-8-hydroxy-10H-1,3-dioxolo[4,5-g]indeno[1,2-b]quinoline,
6,7-(1,4-dioxano)-10H-1,3-dioxolo[4,5-g]indeno[1,2-b]quinoline,
6,7-(1,4-dioxano)-10H-1,3-dioxolo[4,5-g]indeno[1,2-b]quinoline,
7-methoxymethoxy-8-methoxy-10H-1,3-dioxolo[4,5-g]indeno[1,2-b]quinoline,
7-hydroxy-8-methoxy-10H-1,3-dioxolo[4,5-g]indeno[1,2-b]quinoline,
7-(2-aminoethoxy)-8-methoxy-10H-1,3-dioxolo[4,5-g]indeno[1,2-b]quinoline,
7-(2-hydroxyethoxy)-8-methoxy-10H-1,3-dioxolo[4,5-g]indeno[1,2-b]quinoline,
8-methoxy-9-hydroxy-10H-1,3-dioxolo[4,5-g]indeno[1,2-b]quinoline,
(+/−)7-[2(5H)-3,4-dihydro-3-oxyfuranone]-8-methoxy-10H-1,3-dioxolo[4,5-g]indeno[1,2-b]quinoline,
7-n-methylcarbamoyl-8-methoxy-10H-1,3-dioxolo[4,5-g]indeno[1,2-b]quinoline
7-methoxy-8-hydroxy-10H-1,3-dioxolo[4,5-g]indeno[1,2-b]quinoline
7,8-dihydroxy-10H-1,3-dioxolo[4,5-g]indeno[1,2-b]quinoline 8-hydroxy-10H-1,3-dioxolo[4,5-g]indeno[1,2-b]quinoline 2,3-dimethoxy-11H-indeno-8-chloro-[1,2-b]quinoline 2,3-dimethoxy-11H-indeno-[1,2-b]quinolin-8-ol or 2,3-dimethoxy-11H-indeno-8-methoxy-[1,2-b]quinolin-7-ol.

17. A method of claim 13 wherein said mammal is a human.

18. A method of claim 13 wherein said tumor is colon or rectal tumor.

19. A compound of formula (IA)

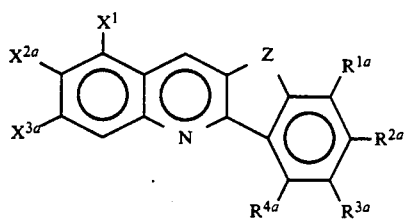

wherein:

$R^{1a}$ is hydrogen, protected hydroxy, F, Cl, Br, I, methoxy or protected amino;

$R^{2a}$ is hydrogen, protected hydroxy, methoxy;

$R^{3a}$ is hydrogen, hydroxy, methoxy, methoxymethoxy, protected amino, —OCONH$_2$, butyrolactone-2-oxy, 2-hydroxyethoxy, 2-aminoethoxy, 3-hydroxypropoxy or 3-aminopropoxy; or taken together with $R^{2a}$ or $R^{4a}$, methylenedioxy or ethylenedioxy;

$R^{4a}$ is hydrogen or protected hydroxy;

Z is —CH$_2$—; and a) $X^1$ is hydrogen; $X^{2a}$ is hydrogen, protected hydroxy, F, Cl, Br, I or methoxy; $X^{3a}$ is hydrogen or protected hydroxy; or b) $X^{2a}$ taken together with $X^{3a}$ is methylenedioxy or ethylenedioxy, and $X^1$ and is hydrogen or a pharmaceutically acceptable salt thereof provided that:

i) at least one of $R^{1a}$ through $R^{3a}$ is other than hydrogen;

ii) when $R^{1a}$ is methoxy, $R^{2a}$ is protected hydroxy or methoxy and $R^{3a}$ is methoxy or hydrogen;

iii) when $R^{2a}$ is protected hydroxy or methoxy, $R^{3a}$ is hydrogen, hydroxy or methoxy, and $R^4$ is hydrogen;

iv) when $R^{4a}$ is protected hydroxy, $R^1$ and $R^3$ are hydrogen and $R^2$ is protected hydroxy; and v) when $R^{1a}$ is fluoro, chloro, iodo or protected amino, $R^2$ is hydrogen, hydroxy or methoxy, $R^{3a}$ is hydrogen, protected hydroxy or methoxy and $R^{4a}$ is hydrogen.

20. A compound of claim 19 which is:

7-methoxy-8-methoxymethoxy-10H-1,3-dioxolo[4,5-g]indeno[1,2-b]quinoline, 7,8-dimethoxymethoxy-10H-1,3-dioxolo[4,5-g]indeno[1,2-b]quinoline, 8-methoxymethoxy-10H-1,3-dioxolo[4,5-g]indeno[1,2-b]quinoline, 2,3-dimethoxy-11H-indeno-8-(4-methoxybenzoxy)-[1,2-b]quinoline, 2,3-dimethoxy-11H-indeno-7-(4-methoxybenzoxy)-8-methoxy-[1,2-b]quinoline, 2,3-dibenzoxy-11H-indeno-8-(4-methoxybenzoxy)-[1,2-b]quinoline, 2-benzoxy-3-methoxy-11H-indeno-8-(4-methoxybenzoxy)-[1,2-b]quinoline, 2-methoxy-3-benzoxy-11H-indeno-8-(4-methoxybenzoxy)-[1,2-b]quinoline, 2-methoxy-11H-indeno-8-(4-methoxybenzoxy)-[1,2-b]quinoline, or 2-benzoxy-11H-indeno-8-(4-methoxybenzoxy)-[1,2-b]quinoline.

* * * * *

UNITED STATES PATENT AND TRADEMARK OFFICE
CERTIFICATE OF CORRECTION

PATENT NO. : 5,223,506
DATED : June 29, 1993
INVENTOR(S) : Luzzio et al.

It is certified that error appears in the above-identified patent and that said Letters Patent is hereby corrected as shown below:

Column 2, line 23, change "inorganic acids such hydrochloride" to --inorganic acids such as hydrochloride--.

Column 2, line 28, change "stearate" to --sterate--.

Column 2, line 69, change "6,7(1,4-dioxano)-" to --6,7-(1,4-dioxano)---.

Column 3, line 6, change "7,8(1,4-dioxano)" to --7,8-(1,4-dioxano)--.

Column 3, line 27, change "2,3-dimethoxy-11" to --2,3-dihydroxy-11--,

Column 4, line 38, change "it is preferable to the protect" to --it is preferable to protect--.

Column 4, line 51, change "Compounds of formula (I) may be convered" to --Compounds of formula (I) may be converted--.

Column 5, line 62, change "7,8 dimethoxy methoxy-10H-1,3-dixolo" to --7,8-dimethoxy methoxy-10H-1,3-dioxolo--.

Column 7, line 24, change "other endocrine gland" to --other endocrine glands--.

Column 8, line 60, change "suitable for parental" to --suitable for parenteral--.

Column 9, line 27, change "1H-300NMR(CDC13);" to --1H-300NMR(CDCl$_3$)--.

Column 10, line 2, change "7-methoxy-10H-1,3-dioxolo[4,5-g]indeno[1,2-g]quinoline" to --7-methoxy-10H-1,3dioxolo[4,5-g]indeno[1,2-b]quinoline--.

Column 10, line 53, change "6[[(4-methylphenyl)mino" to --6[[(4-methylphenyl)imino--.

Column 11, line 20, change "miligrams need" to --milligrams needed--.

Column 11, lines 61-62, change "andydrous ethanol" to --anhydrous ethanol--.

UNITED STATES PATENT AND TRADEMARK OFFICE
CERTIFICATE OF CORRECTION

PATENT NO. : 5,223,506
DATED : June 29, 1993
INVENTOR(S) : Luzzio et al.

It is certified that error appears in the above-identified patent and that said Letters Patent is hereby corrected as shown below:

Column 15, line 59, change "%C calculated 75.50" to --%C calculated 75.70--.

Column 15, line 66, change "except is used that" to --is used except that--.

Column 28, line 2, chance "and $X^1$ and is hydrogen" to --and $X^1$ is hydrogen--.

Signed and Sealed this

Twenty-seventh Day of June, 1995

Attest:

BRUCE LEHMAN

Attesting Officer

Commissioner of Patents and Trademarks